US012560667B2

(12) United States Patent
Ding et al.

(10) Patent No.: US 12,560,667 B2
(45) Date of Patent: Feb. 24, 2026

(54) DYNAMIC PULMONARY MAGNETIC RESONANCE IMAGING METHOD

(71) Applicant: SHANGHAI JIAO TONG UNIVERSITY, Shanghai (CN)

(72) Inventors: Zekang Ding, Shanghai (CN); Huajun She, Shanghai (CN); Yiping Du, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 340 days.

(21) Appl. No.: 18/131,246

(22) Filed: Apr. 5, 2023

(65) Prior Publication Data

US 2024/0329175 A1 Oct. 3, 2024

(30) Foreign Application Priority Data

Mar. 27, 2023 (CN) .......................... 202310308954.8

(51) Int. Cl.
*G01R 33/567* (2006.01)
*A61B 5/055* (2006.01)
(Continued)

(52) U.S. Cl.
CPC .......... *G01R 33/5673* (2013.01); *A61B 5/055* (2013.01); *G01R 33/4816* (2013.01);
(Continued)

(58) Field of Classification Search
CPC ................................................. G01R 33/5673
See application file for complete search history.

(56) References Cited

U.S. PATENT DOCUMENTS

2009/0175523 A1* 7/2009 Chen ..................... G06T 11/006
382/130
2011/0311115 A1* 12/2011 Li ............................. G06T 7/37
382/128
(Continued)

FOREIGN PATENT DOCUMENTS

| CN | 107154065 A | 9/2017 |
| CN | 108447102 A | 8/2018 |
| CN | 110652297 A | 1/2020 |

OTHER PUBLICATIONS

Pang, "Accelerated Whole-Heart Coronary MRA Using motion-corrected Sensitivity Encoding with Three-Dimensional Projection Reconstruction," Magn Reson Med (2015).*
(Continued)

*Primary Examiner* — Hyun D Park
(74) *Attorney, Agent, or Firm* — Fitch, Even, Tabin & Flannery LLP

(57) ABSTRACT
A dynamic pulmonary magnetic resonance imaging method, including: with an ultrashort echo time sequence, acquiring pulmonary magnetic resonance signals in a free-breathing condition; during data acquisition, monitoring a respiratory condition, obtaining a respiration curve; with the respiration curve, performing motion-resolved reconstruction on the acquired pulmonary magnetic resonance data, obtaining motion-resolved lung images; performing motion field estimation on the motion-resolved lung images; performing motion-state weighted motion-compensated reconstruction on results of the motion field estimation, obtaining dynamic pulmonary magnetic resonance images; performing ventilation map estimation on the dynamic pulmonary magnetic resonance images, obtaining a pulmonary ventilation.

18 Claims, 8 Drawing Sheets

(51) Int. Cl.

| | | |
|---|---|---|
| *G01R 33/48* | (2006.01) | |
| *G06T 7/30* | (2017.01) | |
| *G06T 11/00* | (2006.01) | |

(52) U.S. Cl.

CPC ............ *G01R 33/4818* (2013.01); *G06T 7/30* (2017.01); *G06T 11/006* (2013.01); *G06T 11/008* (2013.01)

(56) References Cited

U.S. PATENT DOCUMENTS

| | | | |
|---|---|---|---|
| 2013/0006094 A1* | 1/2013 | Charles ................. | A61B 5/082 600/419 |
| 2016/0073906 A1* | 3/2016 | Fernando ................ | A61B 5/25 600/484 |
| 2016/0324500 A1* | 11/2016 | Fan .................... | G01R 33/5676 |
| 2018/0055414 A1 | 3/2018 | Bieri et al. | |
| 2023/0061960 A1* | 3/2023 | Hung ....................... | G06T 7/35 |

OTHER PUBLICATIONS

Lustig, Michael et al.; "Sparse MRI: The application of compressed sensing for rapid MR imaging"; ResearchGate Jan. 2005; (4 pages).

Thirion, Jean-Philippe; "Image matching as a diffusion process: an analogy with Maxwell's demons"; Med Image Anal. 1998; (19 Pages).

Boyd, Stephen et al.; "Distributed optimization and statistical learning via the alternating direction method of multipliers"; Now Publishers Inc.; 2011(125 pages).

Ding et al., "Dynamic pulmonary MRI using motion-state weighted motion-compensation (MostMoCo) reconstruction with ultrashort TE: A structural and functional study" (2022) Magn Reson Med; vol. 88, No. 1: pp. 224-238.

Kjørstad et al., "Quantitative lung ventilation using Fourier decomposition MRI; comparison and initial study" (2014) Magn Reson Mater Phy; vol. 27, pp. 467-476.

\* cited by examiner

| | |
|---|---|
| S40 | Motion Field Estimation |
| S501 | Motion-State Weighted Motion-Compensated Reconstruction |
| S502 | Moving Image Sequence |

S503

DYNAMIC PULMONARY MAGNETIC RESONANCE IMAGING METHOD

CROSS-REFERENCE TO RELATED APPLICATION

This application claims priority to Chinese Application No. 202310308954.8, filed Mar. 27, 2023, which is incorporated by reference herein in its entirety.

FIELD OF THE INVENTION

The present invention relates to the field of magnetic resonance imaging (MRI) and, in particular, to a dynamic pulmonary MRI method.

DESCRIPTION OF THE PRIOR ART

With the contemporary development of technology, magnetic resonance imaging (MRI) technology has demonstrated the ability to detect pulmonary diseases such as pulmonary embolism, pulmonary nodules and coronavirus disease 2019 (COVID-19). Compared with computed tomography (CT) technology, MRI can provide good soft-tissue contrast and structural information within the lung without ionizing radiation exposure and is therefore more suitable for children and other patients requiring longitudinal follow-up exams. However, most of the existing pulmonary MRI techniques are based on respiratory gating to acquire image data. This approach is associated with low scanning efficiency and can acquire only static image data in a single respiratory condition. Dynamic MRI is a promising technique, which provides high scanning efficiency during examination of lung structure and can be used to assess ventilation function of the lung based on dynamic images. However, dynamic pulmonary MRI is challenging due to a collection of factors including low proton density of the lung, fast signal decay (short $T^*_2$), respiratory motion and variations of signal intensity of the lung parenchyma during respiration.

In order to circumvent the problems of low proton density of the lung and fast signal decay, ultrashort echo time (UTE) sequences are usually used for signal acquisition in pulmonary MRI. Such UTE sequences can capture short $T^*_2$ signals of the lung parenchyma with a sub-millisecond echo time (TE) by applying a readout gradient and starting to collect k-space signals immediately after a radio-frequency (RF) excitation. Some recent studies have demonstrated the possibility of using three-dimensional (3D) radial UTE sequences for the detection of some pulmonary diseases, providing a possible alternative to CT scans. Although the problems with the acquisition of pulmonary magnetic resonance (MR) signals have been satisfactorily addressed by using UTE sequences, pulmonary UTE imaging still relies on accurate respiration monitoring for mitigation of the problem of respiratory artifacts.

There are several methods for respiratory motion monitoring that can be used in MR data acquisition. Clinically, the most commonly used method is to indirectly estimate respiratory motion by measuring abdomen stretching with external devices such as respiratory belts. However, this method requires a cumbersome setup procedure and suffers from inaccurate estimates. Another method is self-navigation, which can be used to estimate respiratory signals directly from acquired k-space data without involving the use of additional devices for respiration monitoring. In this method, self-navigator signals can either be data at the center of k-space or be superior-inferior (SI) navigator echoes. Acquiring a sequence of high temporal resolution and low spatial resolution images can also be used for self-navigation.

There are many motion-corrected or -compensated reconstruction methods that can be used to reconstruct dynamic images from detected respiratory signals. At present, the most commonly used method is motion-resolved reconstruction. In this method, all acquired data are grouped in different motion states, and dynamic images are reconstructed using a compressed sensing (CS) algorithm based on temporal and spatial correlation of an image sequence. This method has been successfully applied to abdominal imaging, cardiac cine imaging, dynamic contrast enhanced MRI and dynamic pulmonary UTE imaging. Representative examples include extra-dimensional golden-angle radial sparse parallel (XD-GRASP) reconstruction and extra-dimensional UTE (XD-UTE) reconstruction. However, this method is prone to blurring artifacts in the event of large motion displacement. To reduce the influence of large motion displacement on motion-resolved reconstruction, some studies have propose reconstruction strategies based on motion compensation (MoCo), which have been applied to dynamic cardiac MRI successfully. Recently, a variant of these MoCo reconstruction strategies, called iterative MoCo (iMoCo) UTE, has been successfully applied to pulmonary UTE MRI. In iMoCo, respiratory motion is modeled by using motion fields derived from registration to transform a single frame of image at a reference state to other motion states. Thus, static images at the reference state are reconstructed, rather than a dynamic sequence of images. However, as CS-based motion-resolved reconstruction and MoCo reconstruction fail to fully take into account the dependence of temporal correlation of dynamic pulmonary MR images on signal intensity of the lung parenchyma, these approaches suffer from reduced quality of reconstructed images.

Therefore, those skilled in the art are directing their effort toward developing a dynamic pulmonary MRI method, which increases temporal correlation among images in a dynamic image sequence by means of motion compensation, reducing reconstruction artifacts. Moreover, it utilizes a motion-state weighting scheme for its adaptation to priori information of signal intensity variation of the lung parenchyma over time, resulting in improved reconstruction quality.

SUMMARY OF THE INVENTION

Compared with dynamic imaging of other parts of the human body, dynamic pulmonary MRI is characterized by decreasing signal intensity of the lung parenchyma in a dynamic image sequence due to decreasing alveolar density from end expiration (EE) to end inspiration (EI). As a result, temporal correlation of dynamic pulmonary MR images decreases with the variation of signal intensity of the lung parenchyma. However, the existing known method based on motion correction or compensation for dynamic pulmonary MRI (e.g., compressed sensing (CS) reconstruction method based on temporal and spatial correlation of an image sequence and motion-compensated reconstruction methods based on iterative MoCo (iMoCo) UTE) fail to fully take into account such signal intensity variation and hence suffer from unsatisfactory quality of reconstructed images.

The present invention provides a dynamic pulmonary MRI method using a motion-compensated reconstruction algorithm for dynamic imaging, which includes 3D radial UTE acquisition, respiratory condition monitoring during data acquisition, motion-resolved reconstruction and motion field estimation, and a novel dynamic MRI reconstruction algorithm. In principle, this algorithm utilizes motion compensation to increase temporal correlation between images in a dynamic image sequence and reduce reconstruction artifacts. Moreover, a motion-state weighting method is used to adapt priori information of signal intensity variation of the lung parenchyma over time, resulting in improved reconstruction quality.

To this end, the present invention provides a dynamic pulmonary magnetic resonance imaging method, comprising:

step S10: with ultrashort echo time sequences, acquiring pulmonary magnetic resonance signals in a free-breathing condition;

step S20: acquiring a respiration curve;

step S30: with the respiration curve, performing motion-resolved reconstruction on data acquired in the step S10, obtaining motion-resolved lung images;

step S40: performing motion field estimation on the motion-resolved lung images;

step S50: performing motion-state weighted motion-compensated reconstruction on results obtained in the step S40, obtaining dynamic pulmonary magnetic resonance images;

step S60: performing ventilation map estimation on the dynamic pulmonary magnetic resonance images, obtaining a pulmonary ventilation.

Further, in the step S10, a sampling trajectory of the ultrashort echo time sequences is in an interleaved spiral phyllotaxis form.

Further, the step S10 comprises: during sampling, rotating each interleave by a golden angle of 137.51° about a Z-axis relative to a previous interleave.

Further, the step S10 further comprises: during data acquisition, monitoring a respiratory condition, wherein the respiratory condition is monitored in a self-navigation manner where before acquisition of each interleave, an echo signal is first acquired in a navigation direction as a navigator signal; or the respiratory condition is monitored with an external respiration monitoring device, and the respiratory condition during acquisition is recorded.

Further, the step S20 comprises:

when the respiratory condition is monitored in the self-navigation manner, performing a one-dimensional inverse Fourier transform on the navigator signal, obtaining projection profiles of coil channels for the pulmonary magnetic resonance signals in the navigation direction;

estimating respiratory signals from the projection profiles of the coil channels; choosing plausible respiratory signals from the respiratory signals;

taking an average of the plausible respiratory signals as a final estimated respiration curve; or when the respiratory condition is monitored with the external respiration monitoring device, directly acquiring the recorded respiration curve from the external respiration monitoring device.

Further, the step S30 comprises:

reconstructing the motion-resolved lung images using a compressed sensing algorithm based on temporal and spatial correlation of an image sequence.

Further, the reconstruction using the compressed sensing algorithm based on temporal and spatial correlation of an image sequence is expressed by the following equation:

$$X = \min_{X} \left\| \sqrt{D} \, (FSX - d) \right\|_2^2 + \lambda_s \|TV_s(X)\|_1 + \lambda_t \|TV_t(X)\|_1 \qquad \text{Equation 1}$$

wherein X is the motion-resolved lung images to be solved, d is k-space data of a multi-channel ultrashort echo time sequence that have been binned into motion states, D is density compensation weights of a non-Cartesian sampling trajectory, S represents coil sensitivity maps, F is a non-uniform fast Fourier transform operator, $TV_t$ and $TV_s$ respectively represent time-domain and space-domain total variation sparsity transformations, $\lambda_t$ and $\lambda_s$ respectively represent weights of time-domain and space-domain sparsity terms.

Further, the Equation 1 is solved using a conjugate gradient algorithm.

Further, the step S40 comprises:

based on the motion-resolved lung images, registering an image at each motion state to images at other motion states, obtaining motion fields of the each motion state to all the other motion states.

Further, an image registration is accomplished using a Demons-based three-dimensional nonrigid image registration technique.

Further, the step S50 comprises:

performing motion-compensated reconstruction with the following equation:

$$X = \min_{X} \left\| \sqrt{D} \, (FSX - d) \right\|_2^2 + \lambda_s \|TV_s(X)\|_1 + \lambda_t \|Ope(X)\|_1 \qquad \text{Equation 2}$$

wherein X is the motion-resolved lung images to be solved, d is k-space data of a multi-channel ultrashort echo time sequence that have been binned into motion states, D is density compensation weights of a non-Cartesian sampling trajectory, S represents coil sensitivity maps, F is a non-uniform fast Fourier transform operator, $\lambda_s$ represents a weight of a space-domain sparsity term, $TV_s$ represents a space-domain total variation sparsity transformation, $\lambda_t$ represents a weight of a time-domain sparsity term, Ope( ) represents a time-domain sparsity transformation, which uses a difference between an image at each motion state and a weighted average image of all other images that are registered to the image at the specific motion state to characterize time-domain sparsity of a dynamic image sequence.

Further, an expression of the Ope( ) is as follows:

$$Ope(X) = x_k - \sum_{\substack{i=1 \\ i \neq k}}^{N} (\alpha_{ik} T_{ik}(x_i)), \, k = 1, 2, \dots N$$

5 where N is the total number of motion states in X, the motion-resolved lung images to be solved, $x_k$ is the k-th motion state in X, $T_{ik}(\ )$ represents a motion transformation operator that transforms an image from a motion state i to a state k, $\alpha_{ik}$ is a motion-state weighting coefficient.

Further, an expression of the motion-state weighting coefficient is as follows:

$$\alpha_{ik} = \frac{c^{-|i-k|}}{\sum_{\substack{t=1 \\ t \neq k}}^{N} c^{-|t-k|}}, \quad c \geq 1$$

where c represents a decay coefficient.

Further, the Equation 2 is solved using an alternating direction method of multipliers.

Further, the step S40 and the step S50 are repeatedly performed.

Further, repeatedly performing the step S40 and the step S50 comprises:

after the motion-state weighted motion-compensated reconstruction is performed on the results obtained in the step S40, obtaining a dynamic pulmonary magnetic resonance image sequence;

based on images with higher quality, repeatedly performing the step S40 on the dynamic pulmonary magnetic resonance image sequence;

repeating the above two steps until an iteration termination criterion is reached.

Further, the step S60 comprises:

estimating the ventilation based on Jacobian determinants.

Further, the step S60 comprises:

registering the dynamic pulmonary magnetic resonance images obtained in the step S50 to an intermediate motion state, obtaining a motion field from each motion state to the intermediate motion state;

calculating a Jacobian determinant for each motion field, obtaining a percentage change in a lung volume from the intermediate motion state to the specific motion state;

fitting a profile of the Jacobian determinant over a breathing cycle to an evolution function of the lung volume and then estimating the ventilation, wherein the evolution function is as follows:

$$v(t) = v_0 - V_r \cos^{2n}\left(\frac{\pi \cdot t}{T_r}\right),$$

where $v_0$ is an end-inspiration volume, $V_r$ is a positive-to-negative peak interval of the lung volume, $T_r$ is the breathing cycle, n is a positive integer that determines a respiration curve form.

Further, the step S60 comprises:

estimating the ventilation based on time-domain variations of signal intensity of the lung parenchyma.

Further, the step S60 comprises:

registering the dynamic pulmonary magnetic resonance images obtained in the step S50 to an intermediate motion state, obtaining a motion field from each motion state to the intermediate motion state;

fitting values of variation of signal intensity over time at each pixel over a breathing cycle to an evolution function of lung density and then estimating the ventilation, wherein the evolution function is as follows:

$$i(t) = i_0 - I_r \cos^{2n}\left(\frac{\pi \cdot t}{T_r}\right),$$

where $i_0$ is end-expiration signal intensity, $I_r$ is a positive-to-negative peak interval of lung signal intensity, $T_r$ is the breathing cycle, n is a positive integer that determines a respiration curve form.

The dynamic pulmonary MRI method of the present invention has the technical benefits as follows:

1. Pulmonary MR signals are acquired with a UTE sequence with SI navigation, dispensing with the need for an external respiration detection device for free-breathing scans of the lung.

2. Acquisition of Pulmonary MR signals in an interleaved spiral phyllotaxis pattern helps reduce artifacts in reconstructed dynamic images.

3. Increasing temporal correlation between images in a dynamic image sequence by motion compensation reduces reconstruction artifacts.

4. Reconstruction quality is improved by adapting priori information of signal intensity variation of the lung parenchyma over time using a motion-state weighted method.

5. With the present application, high-quality lung images and images enabling quantification of ventilation can be obtained under undersampling, reducing the required scanning time. It can also provide 3D visualization of lung structures and the ventilation function.

Below, the concept, structural details and resulting technical effects of the present application will be further described with reference to the accompanying drawings to provide a full understanding of the objects, features and effects of the invention.

DETAILED DESCRIPTION OF THE PREFERRED EMBODIMENTS

Below, the drawings accompanying the specification are referenced to introduce a few preferred embodiments of the present invention so that the techniques thereof become more apparent and readily understood. This invention may be embodied in many different forms of embodiment, and the protection scope thereof is not limited only to the embodiments mentioned herein.

Figure 1:
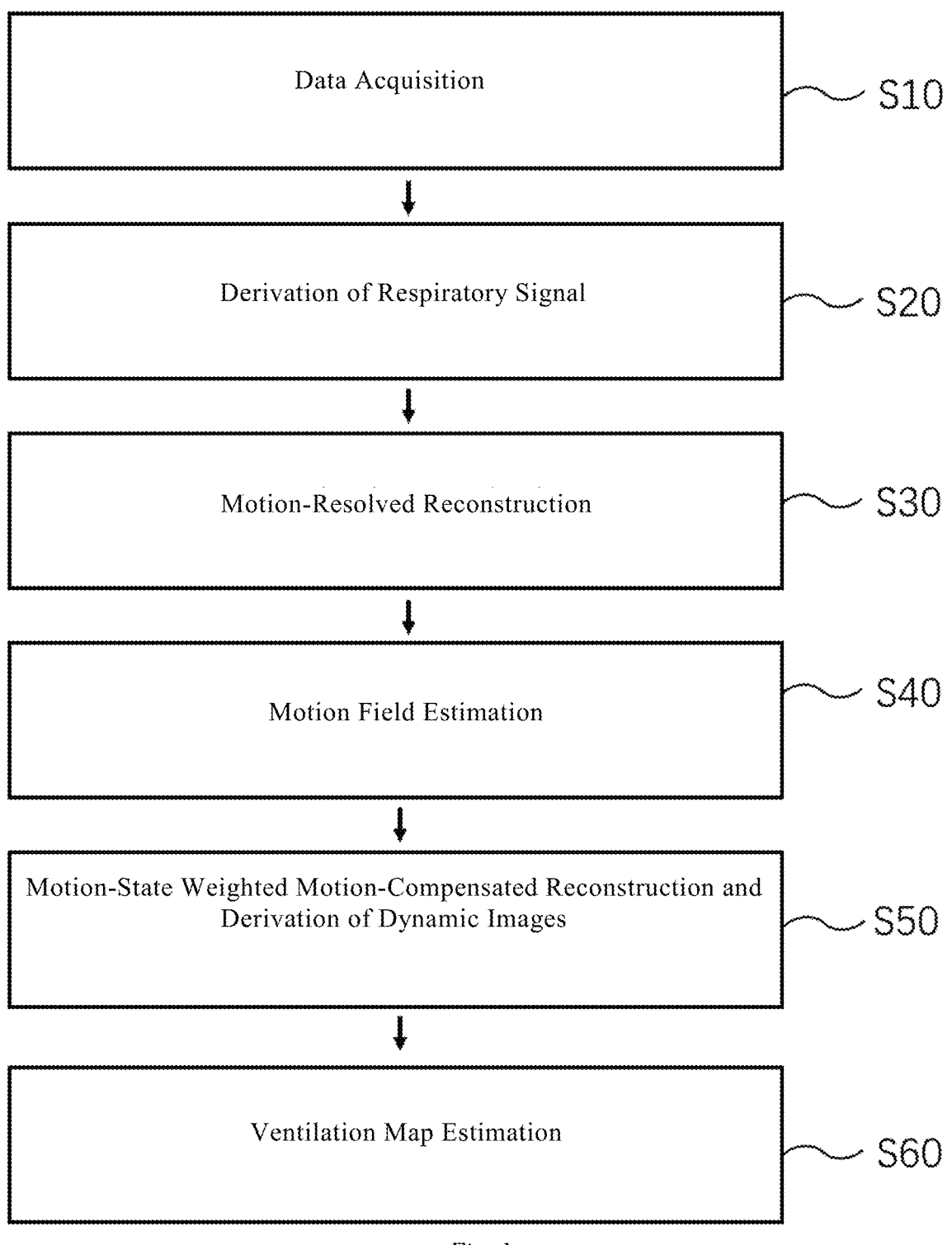
FIG. 1 is a flowchart of a dynamic pulmonary MRI method according to a preferred embodiment of the present invention.
Figure 2:
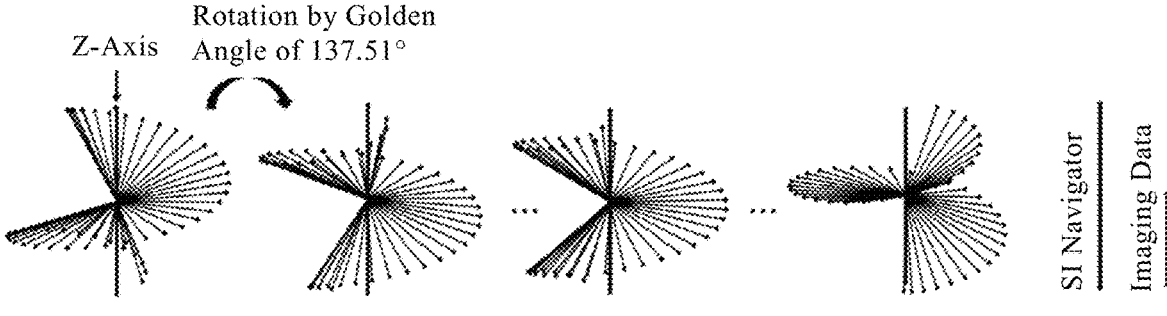
FIG. 2 shows data acquisition with a UTE sequence with SI navigation according to a preferred embodiment of the present invention.

As shown in FIG. 1, a dynamic pulmonary MRI method provided in the present invention includes the steps as follows:

S10: Data acquisition. Data acquisition may be accomplished with an ultrashort echo time (UTE) sequence with navigation, such as a UTE sequence with superior-inferior (SI) navigation. Pulmonary MR signals are acquired in a free-breathing condition. The UTE sequence has a sampling trajectory in the form of an interleaved spiral phyllotaxis pattern, as shown in FIG. 2. The sampling is carried out in such a manner that each interleave is rotated by a golden angle (GA) of 137.51° about the Z-axis relative to the previous one. The GA is defined as $$GA = 360° - \frac{360°}{1.618},$$

where 1.618 is the golden ratio. This sampling scheme ensures random acquisition of each interleave, which helps reduce artifacts in reconstruction of dynamic images. In addition, before the acquisition of each interleave, superior-inferior (SI) echo signals are taken as SI navigators. In some embodiments, an external respiration monitoring device (e.g., respiratory belts) may be used to record respiratory conditions during the acquisition process.

Figure 3:
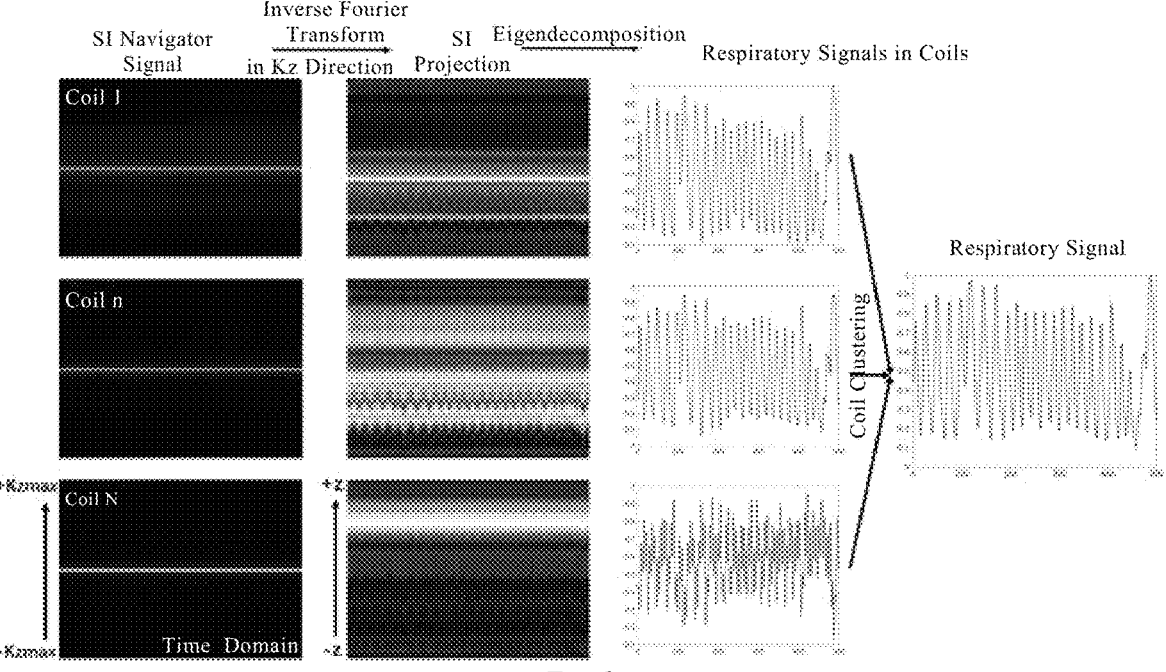
FIG. 3 is a flowchart of a process for extracting a respiration curve from SI navigator signals according to a preferred embodiment of the present invention.
Figure 4:
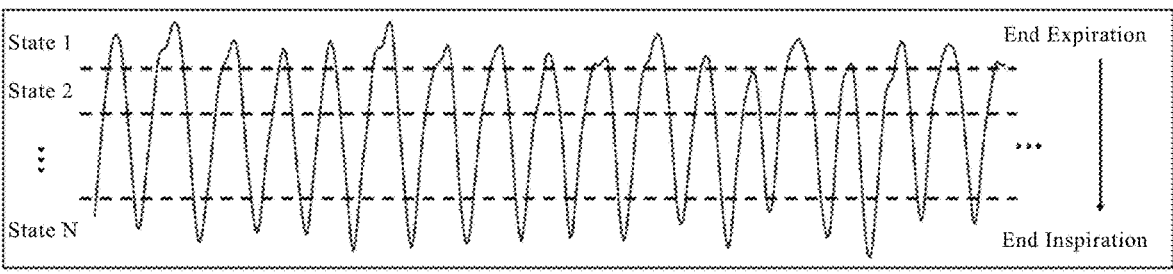
FIG. 4 shows a respiration curve according to a preferred embodiment of the present invention.

S20: Extraction of respiratory signals. From the SI navigator signals in step S10, a respiration curve during the acquisition process is estimated. As shown in FIG. 3, a one-dimensional (1D) inverse Fourier transform is carried out in a Kz direction on the SI navigator signal captured in each coil channel in step S10 (the first column in FIG. 3) to generate a projection profile of the human body signal (i.e., the captured pulmonary MR signal) in each coil channel in the direction of the SI navigator (the second column in FIG. 3). A principal component analysis based algorithm is employed to estimate a respiratory signal from the projection profile of each coil channel. Specifically, the projection profile of each coil channel is eigendecomposed, and a time-domain eigenvector corresponding to the maximum eigenvalue is taken as the respiratory signal of the specific coil channel (the third column in FIG. 3). A coil clustering method is then used to select plausible ones out of the estimated respiratory signals of the coil channels. Specifically, in the coil clustering method, correlation for each pair of the respiration curves of the coil channel is calculated, and every two of the curves with a correlation coefficient higher than 0.95 are considered as plausible respiration curves. As shown in the third column in FIG. 3, as the correlation between the respiration curves of the coils 1 and n is higher than that between the respiration curves of the coils 1 and N, the respiration curves of the coils 1 and n are considered to be more plausible. Finally, an average of the plausible respiration curves is taken as a final estimated respiration curve (the fourth column in FIG. 3). FIG. 4 shows a respiration curve extracted from SI navigator signals captured in a scan.

In some embodiments, when an external respiration monitoring device is used to monitor respiratory conditions, a recorded respiration curve is directly obtained from the external respiration monitoring device.

S30: Motion-resolved reconstruction. Based on the respiration curve of FIG. 4 obtained in step S20, the image data captured in step S10 are binned into N different motion states according to respiratory displacement. Data captured in each single respiratory condition is binned into the same motion state. In this way, k-space data at N different motion states are obtained, as shown in the second column in FIG. 5. At this time, since the k-space data at the motion states are highly undersampled, images with significant undersampling artifacts, as shown in the third column in FIG. 5, will result from direct application of an inverse non-uniform fast Fourier transform (iNUFFT) to them. Therefore, a compressed sensing algorithm based on temporal and spatial correlation of an image sequence is used herein to reconstruct motion-resolved images. The reconstruction can be formulated as the following optimization problem:

$$X = \min_{X} \left\| \sqrt{D} \, (FSX - d) \right\|_2^2 + \lambda_s \|TV_s(X)\|_1 + \lambda_t \|TV_t(X)\|_1 \quad \text{(Eqn. 1)}$$

wherein X denotes motion-resolved lung images to be solve; d, the k-space data of the multi-channel UTE sequence that have been binned into the motion states; D, density compensation weights of the non-Cartesian sampling trajectory; S, coil sensitivity maps; and F, a non-uniform fast Fourier transform (NUFFT) operator. $TV_t$ and $TV_s$ represent total variation (TV) sparsity transformation in the time and space domains with weights $\lambda_t$ and $\lambda_s$, respectively.

Figure 5:
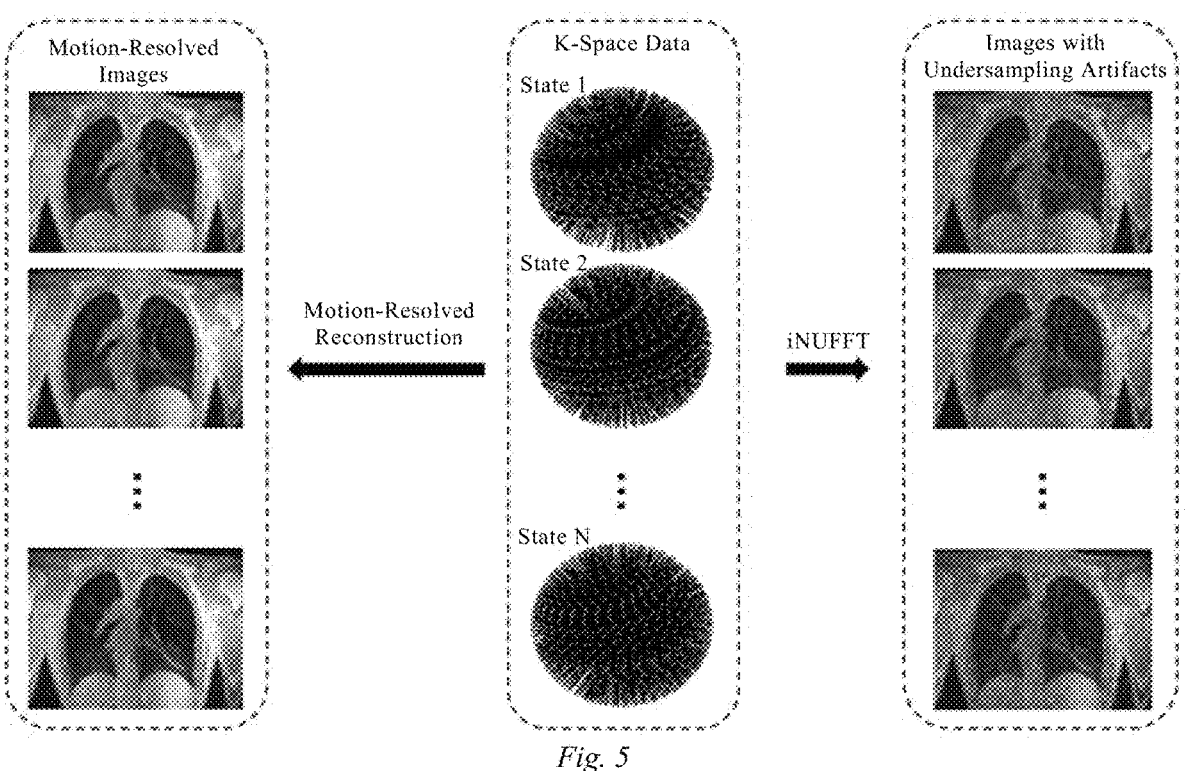
FIG. 5 schematically illustrates motion-resolved reconstruction according to a preferred embodiment of the present invention.

This optimization problem can be solved using a conjugate gradient algorithm, but the quality of the so-obtained motion-resolved lung images is suboptimal, as shown in the first column in the first column in FIG. 5. The conjugate gradient algorithm may be implemented as a conventional algorithm, for example, as taught in the reference: Lustig M, Donoho D, Pauly J M. Sparse MRI: The application of compressed sensing for rapid MR imaging. Magn Reson Med. 2007; 58:1182-95.

Figure 6:
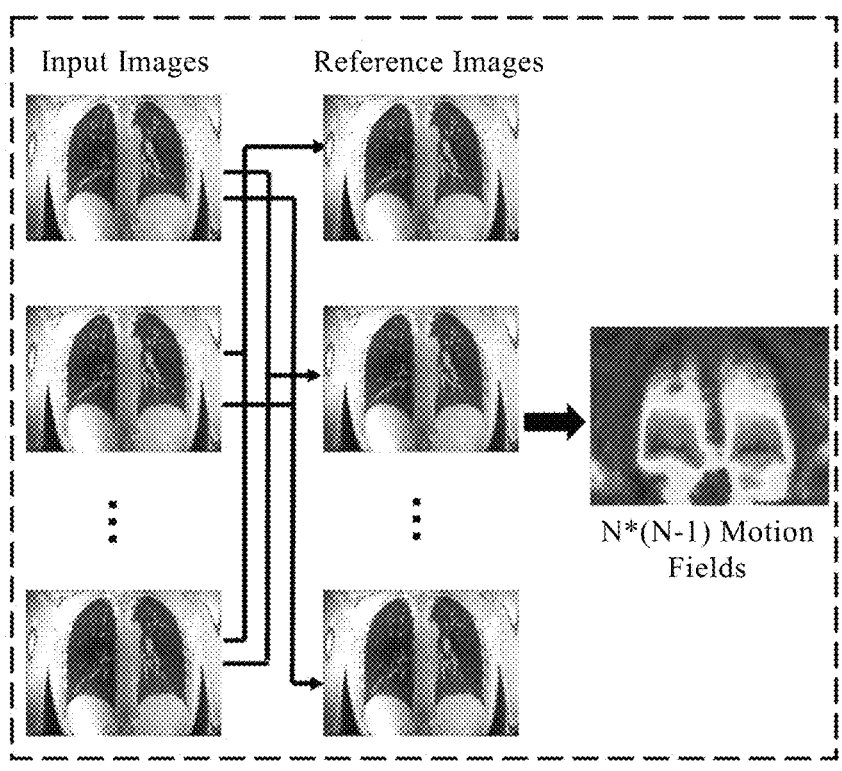
FIG. 6 schematically illustrates motion field estimation according to a preferred embodiment of the present invention.

S40: Motion field estimation. As shown in FIG. 6, based on the motion-resolved images obtained in step S30, an image at each motion state is registered to images at the other (N−1) motion states, resulting in N×(N−1) motion fields for use in the subsequent image reconstruction. The image registration in this step may be accomplished by Demons-based three-dimensional (3D) nonrigid image registration (e.g., using the conventional algorithm taught in the reference: Thirion J P. Image matching as a diffusion process: an analogy with Maxwell's demons. Med Image Anal. 1998; 2:243-60), or another regular 3D nonrigid image registration method.

Figures 7, 8:
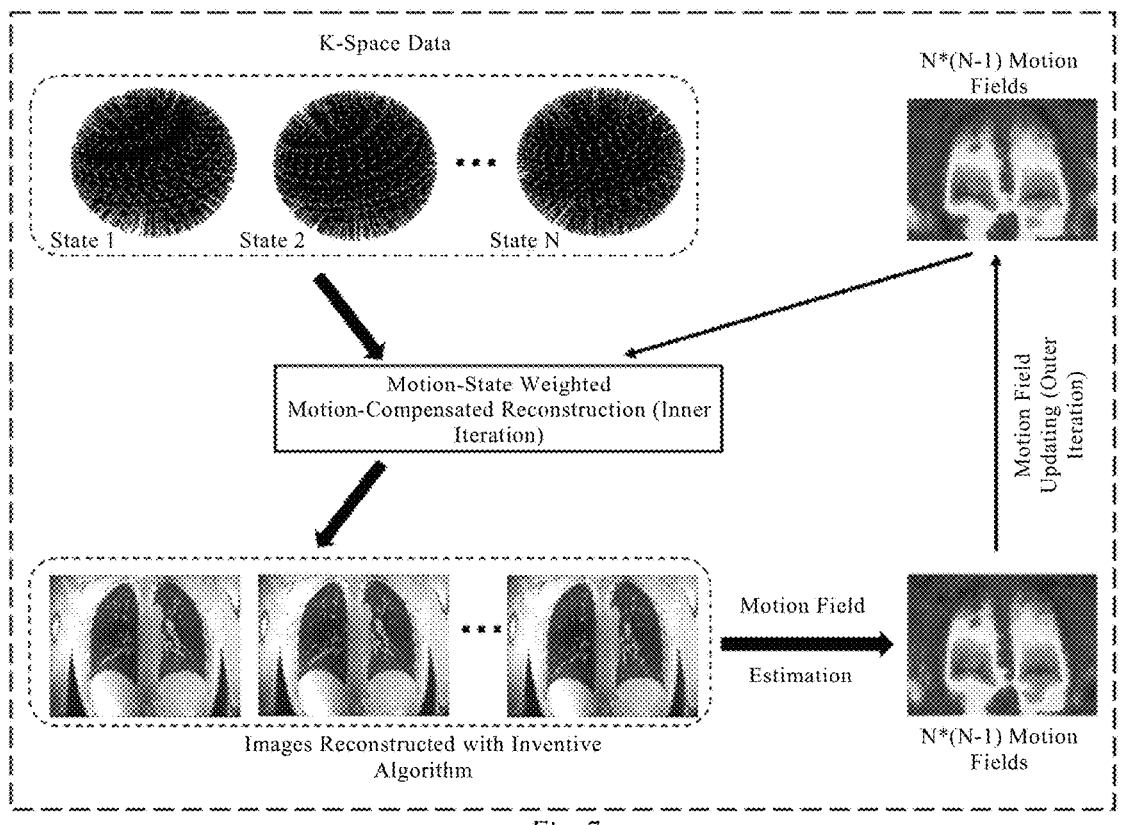
FIG. 7 is a framework diagram of a motion-compensated reconstruction algorithm based on motion-state weighting according to a preferred embodiment of the present invention.
FIG. 8 is a flow diagram of FIG. 7.

S50: Dynamic images are obtained from motion-state weighted, motion-compensated reconstruction. As shown in FIG. 7, dynamic pulmonary MR images are obtained from motion-compensated reconstruction based on the image data that have been binned into the motion states in step S30 and on the motion field obtained in step S40. The motion-compensated reconstruction can be formulated as the following optimization problem:

$$X = \min_{X} \left\| \sqrt{D} \,(FSX - d) \right\|_2^2 + \lambda_s \|TV_s(X)\|_1 + \lambda_t \|Ope(X)\|_1 \qquad \text{(Eqn. 2)}$$

where X, d, D, S and F in the data consistency term (first term) and $\lambda_s$ and $TV_s$ in the spatial sparsity term (second term) are the same notations as those in the problem described in S30 (Eqn. 1). That is, X denotes motion-resolved lung images to be solve; d, the k-space data of the multi-channel UTE sequence that have been binned into the motion states; D density compensation weights of the non-Cartesian sampling trajectory; S, coil sensitivity maps; F, a non-uniform fast Fourier transform operator; $\lambda_s$, a weight of the space-domain sparsity term; and $TV_s$, sparsity transformation in the space domain. $\lambda_t$ in the time-domain sparsity term (third term) is a weight of this time-domain sparsity term, and Ope( ) represents sparsity transformation in the time domain. This transformation determines the difference between the image at each motion state and a weighted average image of all other images registered thereto as the time-domain sparsity of the dynamic image sequence. Ope( ) is expressed as (Eqn. 3):

$$Ope(X) = x_k - \sum_{\substack{i=1 \\ i \neq k}}^{N} (\alpha_{ik} T_{ik}(x_i)), \; k = 1, 2, \ldots N$$

where N is the total number of motion states in X, $x_k$ is the k-th motion state in X, and $T_{ik}(\;)$ is a motion transformation operator that transforms an image from the i-th motion state to the k-th state. $\alpha_{ik}$ is a motion-state weighting coefficient defined as (Eqn. 4):

$$\alpha_{ik} = \frac{c^{-|i-k|}}{\sum_{\substack{t=1 \\ t \neq k}}^{N} c^{-|t-k|}}, \; c \geq 1$$

For the k-th motion state, the coefficient $\alpha_{ik}$ decreases with an increase in a time-domain distance between $x_i$ and $x_k$ at a rate determined by a decay coefficient c. The motion-compensation optimization problem is solved using an alternating direction method of multipliers (ADMM), and dynamic pulmonary MR images are obtained. The ADMM may be a conventional method, such as that taught in the reference: Boyd SP. Distributed optimization and statistical learning via the alternating direction method of multipliers. Now Publishers Inc.; 2011:126 p.

In some preferred embodiments, image reconstruction quality can be improved by repeated iterations. As shown in FIGS. 7 and 8, steps S40 and S50 may be repeated. Specifically, step S50 may further include: (S501) motion-state weighted, motion-compensated reconstruction, i.e., the derivation of dynamic images using Eqns. 2, 3 and 4; and (S502) after the sequence of dynamic images is obtained, re-estimating motion fields based on these images with higher quality (step S40), as shown in S503. Through iterating the reconstruction and motion field estimation steps, higher motion field estimation accuracy and improved image reconstruction quality can be obtained. The iteration process may be stopped when a criterion predefined according to the actual need is met, such as a particular number of iterations, or a predetermined level of image quality.

Figure 9:
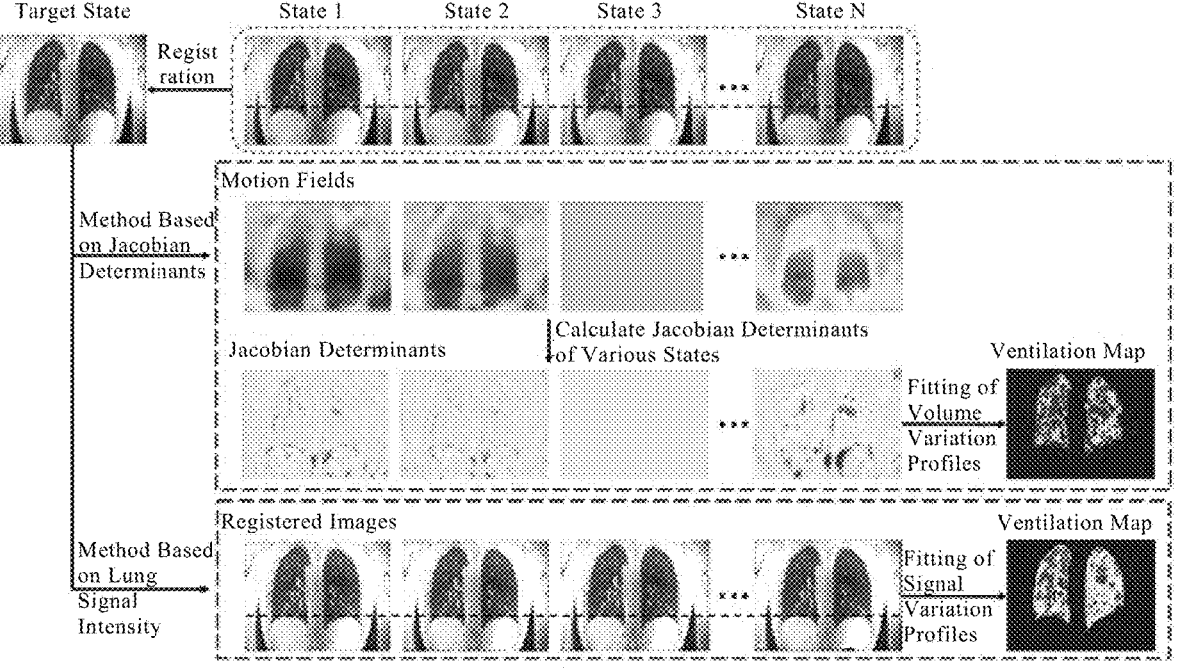
FIG. 9 schematically illustrates ventilation estimation according to a preferred embodiment of the present invention.

S60: estimation of ventilation map. A pulmonary ventilation map is estimated from the dynamic pulmonary images obtained in step S50. Alveolar volume varies during breathing. Motion fields associated with such variation can be estimated from the dynamic images. The Jacobian determinants of the motion fields represent percentage changes of alveolar volume (see FIG. 9). In this way, a ventilation value of the lung can be estimated. In addition, the variation of alveolar volume during breathing leads to variation of alveolar density, which is reflected by variation of signal intensity of the lung parenchyma in the magnetic resonance images. The ventilation value of the lung can also be estimated from such variation of signal intensity, as shown in FIG. 9.

Estimation of ventilation based on Jacobian determinants. As shown in FIG. 9, the dynamic images are registered to a chosen intermediate motion state (e.g., the N/2-th motion state), deriving a motion field from each motion state to the intermediate state. The intermediate motion state may be chosen as any of the first to N-th motion states, with the N/2-th motion state being preferred. The Jacobian determinant of each motion field is then calculated, and a percentage change in lung volume from the intermediate state to each motion state is determined. The Jacobian determinants are calculated according to (Eqn. 5):

$$J(x, y, z) = \begin{vmatrix} \dfrac{\partial x'}{\partial x} & \dfrac{\partial x'}{\partial y} & \dfrac{\partial x'}{\partial z} \\[2mm] \dfrac{\partial y'}{\partial x} & \dfrac{\partial y'}{\partial y} & \dfrac{\partial y'}{\partial z} \\[2mm] \dfrac{\partial z'}{\partial x} & \dfrac{\partial z'}{\partial y} & \dfrac{\partial z'}{\partial z} \end{vmatrix} = \begin{vmatrix} \dfrac{\partial u_x}{\partial x} + 1 & \dfrac{\partial u_x}{\partial y} & \dfrac{\partial u_x}{\partial z} \\[2mm] \dfrac{\partial u_y}{\partial x} & \dfrac{\partial u_y}{\partial y} + 1 & \dfrac{\partial u_y}{\partial z} \\[2mm] \dfrac{\partial u_z}{\partial x} & \dfrac{\partial u_z}{\partial y} & \dfrac{\partial u_z}{\partial z} + 1 \end{vmatrix},$$

where $(u_x, u_x, u_x)$ represents displacement of each voxel derived from the registration. To take full advantage of information of all the motion states and minimize the influence of noise, the Jacobian determinant profile over the breathing cycle is fitted to an evolution function of the lung volume (Eqn. 6):

$$v(t) = v_0 - V_r \cos^{2n}\!\left( \frac{\pi \cdot t}{T_r} \right),$$

where $v_0$ is a maximum volume (end-inspiration volume), $V_r$ is a positive-to-negative peak interval of the lung volume, $T_r$ is the breathing cycle and n is a positive integer that determines the form of the respiration curve. According to this evolution function, the maximum volume $v_0$ and the positive-to-negative peak interval $V_r$ are fitted, and the pulmonary ventilation can be estimated as $V_r/v_0$.

Estimation of ventilation based on signal intensity in lung images. Similar to the method based on Jacobian determinants, as shown in FIG. 9, the dynamic images are registered to an intermediate motion state, and variation of signal intensity over time at each pixel in the breathing cycle is then fitted to the lung density, i.e., an evolution function of signal intensity in pulmonary MR (Eqn. 7):

$$i(t) = i_0 - I_r \cos^{2n}\left(\frac{\pi \cdot t}{T_r}\right),$$

where $i_0$ is maximum signal intensity (end-expiration signal intensity), and $I_r$ is an positive-to-negative peak interval of lung signal intensity. According to this evolution function, the maximum signal intensity $i_0$ and the positive-to-negative peak interval $I_r$ are fitted, and the pulmonary ventilation can be estimated as $I_r/i_0$.

In vitro porcine lung imaging and free-breathing human lung imaging tests were carried out in accordance with the preferred embodiments of the present invention on a 3.0 Tesla medical MRI system (uMR790, Shanghai United Imaging Healthcare Co., Ltd.). These tests confirmed the feasibility of dynamic pulmonary imaging according to the foregoing preferred embodiments of the present invention.

Figure 10:
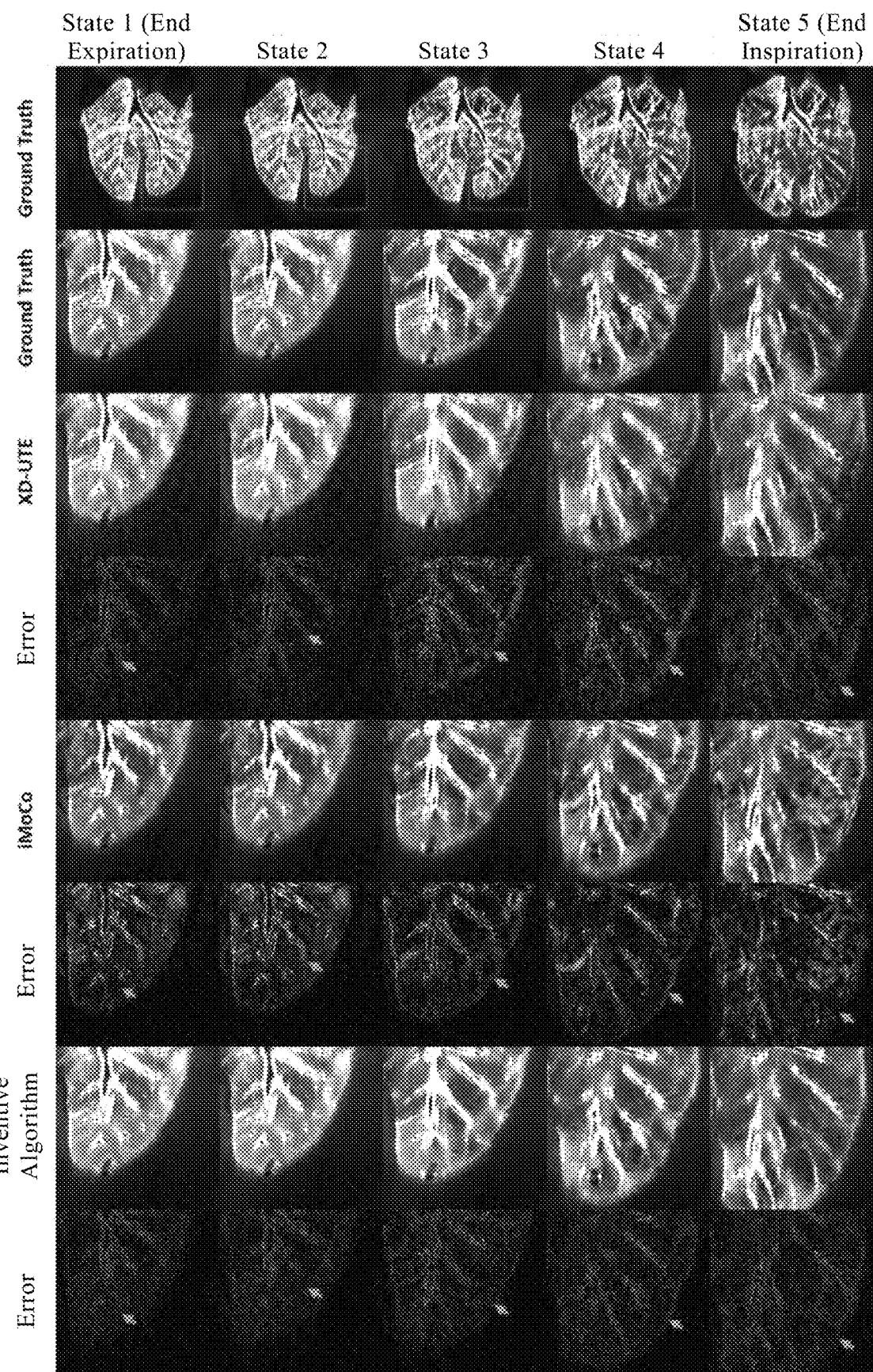
FIG. 10 shows the results of an imaging test performed on an in vitro porcine lung according to a preferred embodiment of the present invention.

FIG. 10 shows the results of the in vitro porcine lung imaging test. In order to acquire fully sampled data of the in vitro porcine lung in different respiratory conditions different amounts of air (0 ml, 200 ml, 400 ml, 600 ml, 800 ml) were pumped into the porcine lung using an inflator. Static scans were then performed on the porcine lung at the various states, and fully sampled data were acquired. The scan parameters were as follows: field of view (FoV)=32×14×32 cm³; isotropic resolution=0.8 mm; flip angle=8°; readout bandwidth=250 Hz/pixel; echo time (TE)=60 µs; repetition time=3 ms. A total of 220,000 spokes including 4,400 interleaves with 50 spokes each were acquired in 11 min and 17 s for each motion state. After the fully sampled data were acquired, the data at each motion state were subjected to 10-fold retrospective undersampling. Reconstruction was conducted based on the undersampled data using different reconstruction methods, and the results are shown in FIG. 10.

In FIG. 10, ground truth images reconstructed from the fully sampled k-space data are shown in the first row as references, and enlarged views of the portions of the images in the first row encircled by the squares are shown in the second row. Ground truth images reconstructed based on motion-resolved reconstruction (XD-UTE) are shown in the third row as references, and error maps of the images in the third row are shown in the fourth row. Ground truth images reconstructed based on iMoCo are shown in the fifth row as references, and error maps of the images in the fifth row are shown in the sixth row. Ground truth images reconstructed according to the method of the present invention are shown in the seventh row, and error maps of the images in the seventh row are shown in the eighth row. Decreasing signal intensity of the lung parenchyma caused by decreasing alveolar density from end expiration (EE) to end inspiration (EI) can be observed obviously. Image blurring at some tracheal structures and the edge of porcine lung are observed in the XD-UTE images (third row), as indicated by the green arrows in the error maps. Such image blurring is substantially reduced in the iMoCo results (fifth row). However, time-domain variations of signal intensity of the lung parenchyma are substantially reduced in the iMoCo reconstructed images, and obvious reconstruction errors are observed in the iMoCo error maps (sixth row). Overall, the inventive reconstruction algorithm better preserves time-domain variation signal intensity of the lung parenchyma compared to iMoCo, and results in reduced random noise, sharper tracheal structures and sharper lung edges than XD-UTE.

Figure 11:
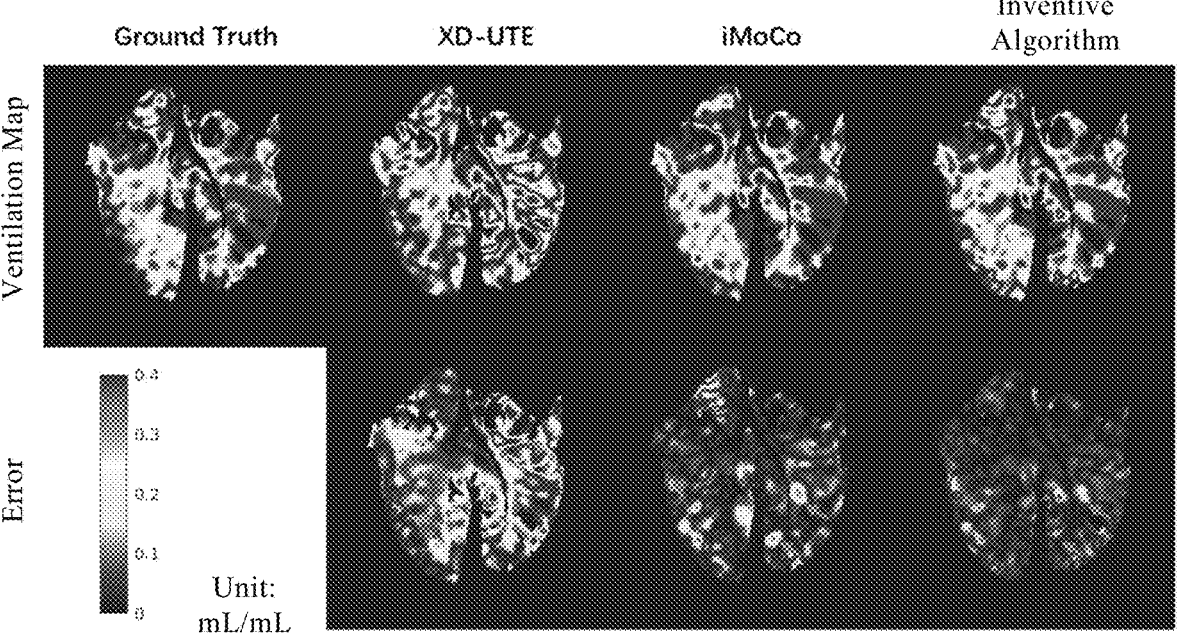
FIG. 11 shows the results of ventilation map estimation of the in vitro porcine lung according to a preferred embodiment of the present invention.

FIG. 11 shows ventilation maps estimated from the dynamic porcine lung images of FIG. 10 using the method based on Jacobian determinants. The ventilation maps estimated from the ground truth, XD-UTE, iMoCo and inventive reconstruction algorithm images are shown in the first row, and error maps between ventilation maps derived from different images and the ground truth images are shown in the second row. Compared with the other two methods, the ventilation maps of the inventive reconstruction algorithm show reduced estimation errors, as indicated by the red arrows.

Figures 12, 13:
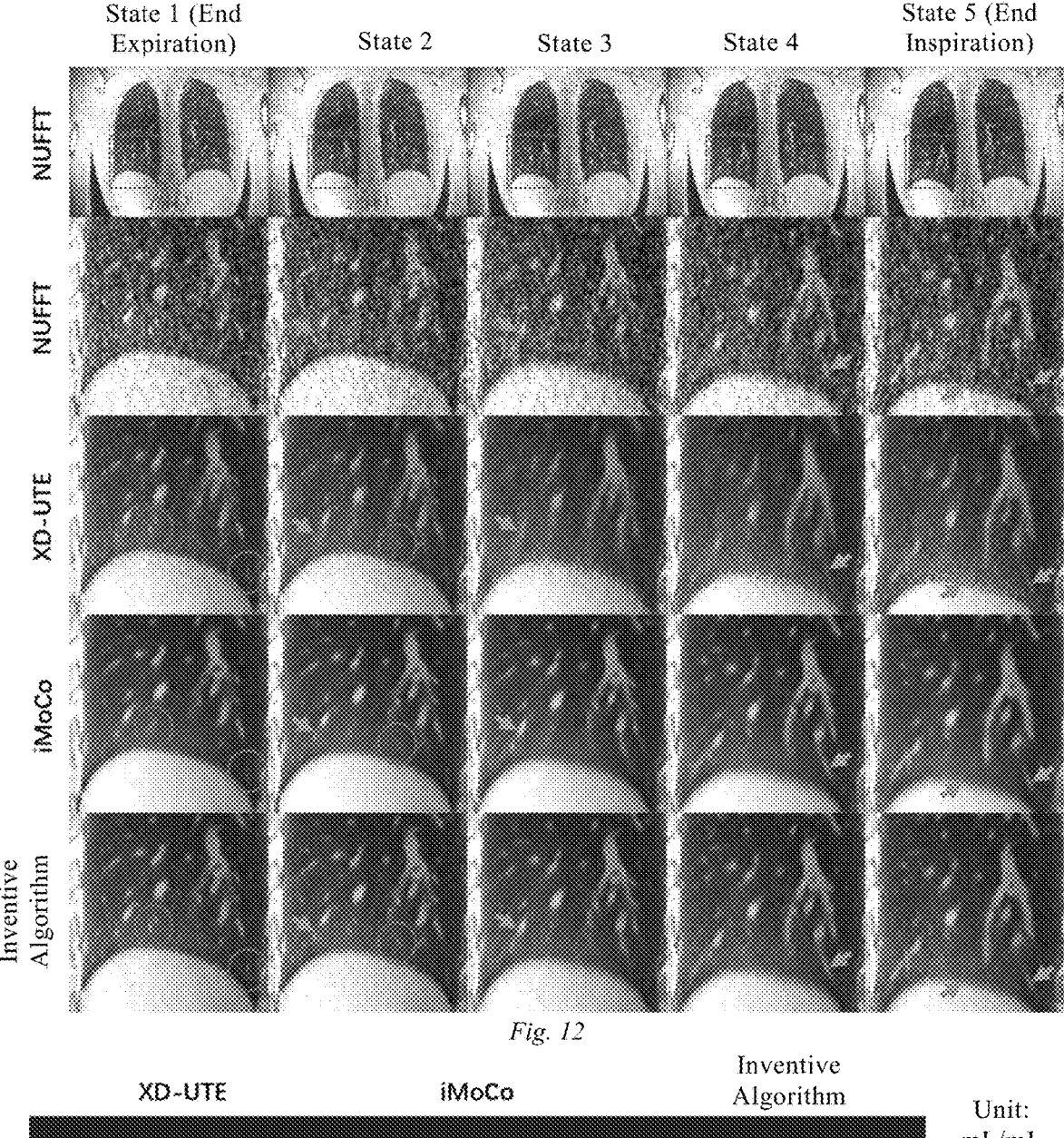
FIG. 12 shows the results of a free-breathing dynamic imaging test performed on human lungs according to a preferred embodiment of the present invention.
FIG. 13 shows the results of ventilation map estimation of the human lungs according to a preferred embodiment of the present invention.

FIG. 12 shows the result of the free-breathing human lung imaging test. The scan parameters for human lung imaging were as follows: FoV=40×28×30 cm³; isotropic resolution=0.8 mm; flip angle=4°; readout bandwidth=250 Hz/pixel; TE=60 µs; repetition time=3 ms. For human lung imaging, a total of 200,000 spokes were acquired in approximate 10 min, including 4,000 interleaves with 50 imaging spokes and one SI navigator each. The reconstruction results of different reconstruction methods are shown in FIG. 12.

In FIG. 12, images directly obtained from NUFFT of highly undersampled data at different motion states are shown in the first row, and enlarged views of the NUFFT, XD-UTE, iMoCo and inventive reconstruction algorithm results in the portions encircled by the squares in the first row are shown in the other rows. There are severe undersampling artifacts in the NUFFT images, and these artifacts are reduced in the XD-UTE images. However, image blurring of some pulmonary structures and diaphragm areas are observed in the XD-UTE images, as indicated by the green arrows. Such residual noise and image blurring are mitigated in the iMoCo images, which, however, appear oversmoothed, especially because some parenchyma structures indicated by the red circles are blurred. The results of the inventive reconstruction algorithm have better lung parenchyma contrast than the iMoCo results and show comparable sharpness of pulmonary structures and the diaphragm with the iMoCo results.

FIG. 13 shows ventilation maps estimated from the dynamic human lung images of FIG. 12 using the method based on Jacobian determinants. In line with the assessment of the porcine lung ventilation maps shown in FIG. 11, the human lung ventilation maps derived from the inventive reconstruction algorithm are more photorealistic than those of XD-UTE.

Preferred specific embodiments of the present invention have been described in detail above. It is to be understood that, those of ordinary skill in the art can make various modifications and changes based on the concept of the present invention without exerting any creative effort. Accordingly, all the technical solutions that can be obtained by those skilled in the art by logical analysis, inference or limited experimentation in accordance with the concept of the present invention on the basis of the prior art are intended to fall within the protection scope as defined by the claims.

The invention claimed is:

1. A dynamic pulmonary magnetic resonance imaging method, comprising:
  step S10: with ultrashort echo time sequences, acquiring pulmonary magnetic resonance signals in a free-breathing condition;

step S20: acquiring a respiration curve;

step S30: with the respiration curve, performing motion-resolved reconstruction on data acquired in the step S10, obtaining motion-resolved lung images;

step S40: performing motion field estimation on the motion-resolved lung images;

step S50: performing motion-state weighted motion-compensated reconstruction on results obtained in the step S40, obtaining dynamic pulmonary magnetic resonance images;

step S60: performing ventilation map estimation on the dynamic pulmonary magnetic resonance images, obtaining a pulmonary ventilation;

wherein the step S30 comprises:

reconstructing the motion-resolved lung images using a compressed sensing algorithm based on temporal and spatial correlation of an image sequence;

wherein the reconstruction using the compressed sensing algorithm based on temporal and spatial correlation of an image sequence is expressed by the following equation:

$$X = \min_{X}\left\|\sqrt{D}\,(FSX - d)\right\|_2^2 + \lambda_s\|TV_s(X)\|_1 + \lambda_t\|TV_t(X)\|_1 \qquad \text{Equation 1}$$

wherein X is the motion-resolved lung images to be solved, d is k-space data of a multi-channel ultrashort echo time sequence that have been binned into motion states, D is density compensation weights of a non-Cartesian sampling trajectory, S represents coil sensitivity maps, F is a non-uniform fast Fourier transform operator, $TV_t$ and $TV_s$ respectively represent time-domain and space-domain total variation sparsity transformations, $\lambda_t$ and $\lambda_s$ respectively represent weights of time-domain and space-domain sparsity terms.

2. The dynamic pulmonary magnetic resonance imaging method of claim 1, wherein in the step S10, a sampling trajectory of the ultrashort echo time sequences are in an interleaved spiral phyllotaxis form.

3. The dynamic pulmonary magnetic resonance imaging method of claim 2, wherein the step S10 comprises:

during sampling, rotating each interleave by a golden angle of 137.51° about a Z-axis relative to a previous interleave.

4. The dynamic pulmonary magnetic resonance imaging method of claim 2, wherein the step S10 further comprises:

during data acquisition, monitoring a respiratory condition, wherein the respiratory condition is monitored in a self-navigation manner where before acquisition of each interleave, an echo signal is first acquired in a navigation direction as a navigator signal; or the respiratory condition is monitored with an external respiration monitoring device, and the respiratory condition during acquisition is recorded.

5. The dynamic pulmonary magnetic resonance imaging method of claim 4, wherein the step S20 comprises:

when the respiratory condition is monitored in the self-navigation manner, performing a one-dimensional inverse Fourier transform on the navigator signal, obtaining projection profiles of coil channels for the pulmonary magnetic resonance signals in the navigation direction;

estimating respiratory signals from the projection profiles of the coil channels;

choosing plausible respiratory signals from the respiratory signals;

taking an average of the plausible respiratory signals as a final estimated respiration curve; or when the respiratory condition is monitored with the external respiration monitoring device, directly acquiring a recorded respiration curve from the external respiration monitoring device.

6. The dynamic pulmonary magnetic resonance imaging method of claim 1, wherein the Equation 1 is solved using a conjugate gradient algorithm.

7. The dynamic pulmonary magnetic resonance imaging method of claim 1, wherein the step S40 comprises:

based on the motion-resolved lung images, registering an image at each motion state to images at other motion states, obtaining motion fields of the each motion state to all the other motion states.

8. The dynamic pulmonary magnetic resonance imaging method of claim 7, wherein an image registration is accomplished using a Demons-based three-dimensional nonrigid image registration technique.

9. The dynamic pulmonary magnetic resonance imaging method of claim 1, wherein the step S50 comprises:

performing motion-compensated reconstruction with the following equation:

$$X = \min_{X}\left\|\sqrt{D}\,(FSX - d)\right\|_2^2 + \lambda_s\|TV_s(X)\|_1 + \lambda_t\|Ope(X)\|_1 \qquad \text{Equation 2}$$

wherein X is the motion-resolved lung images to be solved, d is k-space data of a multi-channel ultrashort echo time sequence that have been binned into motion states, D is density compensation weights of a non-Cartesian sampling trajectory, S represents coil sensitivity maps, F is a non-uniform fast Fourier transform operator, $\lambda_s$ represents a weight of a space-domain sparsity term, $TV_s$ represents a space-domain total variation sparsity transformation, $\lambda_t$ represents a weight of a time-domain sparsity term, Ope( ) represents a time-domain sparsity transformation, which uses a difference between an image at each motion state and a weighted average image of all other images that are registered to the image at the specific motion state to characterize time-domain sparsity of a dynamic image sequence.

10. The dynamic pulmonary magnetic resonance imaging method of claim 9, wherein an expression of the Ope( ) is as follows:

$$Ope(X) = x_k - \sum_{\substack{i=1 \\ i \neq k}}^{N} (\alpha_{ik} T_{ik}(x_i)), \; k = 1, 2, \ldots N$$

where N is the total number of motion states in X, the motion-resolved lung images to be solved, $x_k$ is the k-th motion state in X, $T_{ik}( )$ represents a motion transformation operator that transforms an image from a motion state i to a state k, $\alpha_{ik}$ is a motion-state weighting coefficient.

11. The dynamic pulmonary magnetic resonance imaging method of claim 10, wherein an expression of the motion-state weighting coefficient is as follows:

$$\alpha_{ik} = \frac{c^{-|i-k|}}{\sum_{\substack{t=1 \\ t \neq k}}^{N} c^{-|t-k|}}, c \geq 1$$

where c represents a decay coefficient.

12. The dynamic pulmonary magnetic resonance imaging method of claim 11, wherein the Equation 2 is solved using an alternating direction method of multipliers.

13. The dynamic pulmonary magnetic resonance imaging method of claim 1, wherein the step S40 and the step S50 are repeatedly performed.

14. The dynamic pulmonary magnetic resonance imaging method of claim 13, wherein repeatedly performing the step S40 and the step S50 comprises:

after the motion-state weighted motion-compensated reconstruction is performed on the results obtained in the step S40, obtaining a dynamic pulmonary magnetic resonance image sequence;

with images with higher quality, repeatedly performing the step S40 on the dynamic pulmonary magnetic resonance image sequence;

repeating the above two steps until an iteration termination criterion is reached.

15. The dynamic pulmonary magnetic resonance imaging method of claim 1, wherein the step S60 comprises:

estimating the ventilation based on Jacobian determinants.

16. The dynamic pulmonary magnetic resonance imaging method of claim 15, wherein the step S60 comprises:

registering the dynamic pulmonary magnetic resonance images obtained in the step S50 to an intermediate motion state, obtaining a motion field from each motion state to the intermediate motion state;

calculating a Jacobian determinant for each motion field, obtaining a percentage change in a lung volume from the intermediate motion state to the specific motion state;

fitting a profile of the Jacobian determinant over a breathing cycle to an evolution function of the lung volume and then estimating the ventilation, wherein the evolution function is as follows:

$$v(t) = v_0 - V_r \cos^{2n}\left(\frac{\pi \cdot t}{T_r}\right),$$

where $v_0$ is an end-inspiration volume, $V_r$ is a positive-to-negative peak interval of the lung volume, $T_r$ is the breathing cycle, n is a positive integer that determines a respiration curve form.

17. The dynamic pulmonary magnetic resonance imaging method of claim 1, wherein the step S60 comprises:

estimating the ventilation based on time-domain variations of signal intensity of a lung parenchyma.

18. The dynamic pulmonary magnetic resonance imaging method of claim 17, wherein the step S60 comprises:

registering the dynamic pulmonary magnetic resonance images obtained in the step S50 to an intermediate motion state, obtaining a motion field from each motion state to the intermediate motion state;

fitting values of variation of signal intensity over time at each pixel over a breathing cycle to an evolution function of lung density and then estimating the ventilation, wherein the evolution function is as follows:

$$i(t) = i_0 - I_r \cos^{2n}\left(\frac{\pi \cdot t}{T_r}\right),$$

where $i_0$ is end-expiration signal intensity, $I_r$ is a positive-to-negative peak interval of lung signal intensity, $T_r$ is the breathing cycle, n is a positive integer that determines a respiration curve form.

\* \* \* \* \*